United States Patent [19]

Henrick et al.

[11] 4,224,330

[45] Sep. 23, 1980

[54] ESTERS AND THIOLESTERS OF BENZOTHIENYL ACIDS

[75] Inventors: Clive A. Henrick; Jeffrey N. Labovitz, both of Palo Alto; Michael M. Leippe, Boulder Creek; Sam L. Woo, Redwood City, all of Calif.

[73] Assignee: Zoecon Corporation, Palo Alto, Calif.

[21] Appl. No.: 74,850

[22] Filed: Sep. 13, 1979

[51] Int. Cl.³ .................... A01N 43/40; A01N 43/36; A01N 43/10; C07D 409/02

[52] U.S. Cl. .................................. 424/263; 424/274; 424/275; 260/326.5 R; 260/326.5 S; 546/274; 549/58

[58] Field of Search .................... 546/274; 549/58; 260/326.5 S; 260/326.5 R; 424/275, 274, 263

[56] References Cited

U.S. PATENT DOCUMENTS

| 3,751,416 | 8/1973 | Allen et al. | 260/326.5 R |
| 4,163,787 | 8/1979 | Malhotra et al. | 260/326.5 R |

FOREIGN PATENT DOCUMENTS

| 2812169 | 10/1978 | Fed. Rep. of Germany | 260/326.5 R |
| 2843760 | 4/1979 | Fed. Rep. of Germany | 260/326.5 R |

*Primary Examiner*—John D. Randolph
*Assistant Examiner*—Robert C. Whittenbaugh

[57] ABSTRACT

Esters and thiolesters of benzothienyl acids, intermediates thereof, synthesis thereof, and the use thereof for the control of pests.

28 Claims, No Drawings

ESTERS AND THIOLESTERS OF BENZOTHIENYL ACIDS

This invention relates to novel esters and thiolesters of benzothienyl acids, novel intermediate therefor, synthesis thereof and the control of pests.

The esters and thiolesters of the present invention are represented by the following formula (A):

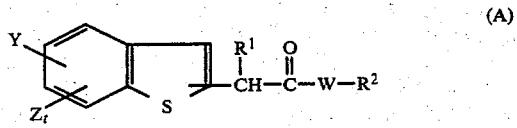

wherein,

W is oxygen or sulfur; t is zero, one, two, or three; each of Y and Z is, independently, selected from hydrogen, bromo, chloro, fluoro, lower alkyl, lower alkoxy, lower halo-alkoxy and lower haloalkyl; $R^1$ is lower alkyl, lower alkenyl or lower cycloalkyl;

$R^2$ is selected from the groups,

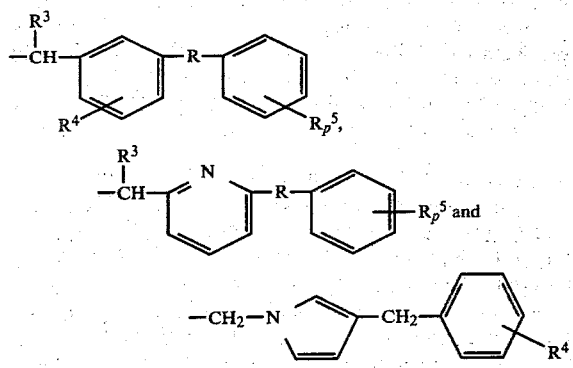

R is oxygen, sulfur, methylene or carbonyl;
$R^3$ is hydrogen, cyano, ethynyl, methyl, ethyl, or trifluoromethyl;
$R^4$ is hydrogen or fluoro;
$R^5$ is hydrogen, bromo, chloro, fluoro, methyl, methoxy, or trifluoromethyl; and p is zero, one or two.

The compounds of the present invention represented by formula (A) are useful agents for the control of pests such as insects and acarids.

In the description hereinafter and the appended claims, each of R through $R^5$, W, Y, Z, p and t is as defined hereinabove, unless otherwise specified.

The compounds of formula (A) wherein W is oxygen can be synthesized by esterification of an acid of formula (I) with an alcohol of formula II, III or IV.

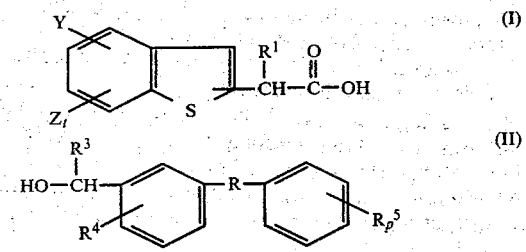

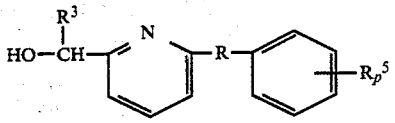

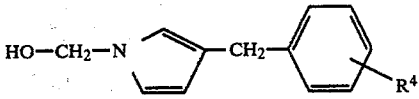

The esterification can be carried out by reaction of an acid of formula I, salt thereof or the acid halide with an alcohol of formula II, III or IV to form a carboxylic ester of formula A. For example, an acid chloride of the acid of formula I is reacted with an alcohol of formula II, III or IV in an organic solvent such as diethyl ether, benzene, tetrahydrofuran (THF), dimethylformamide (DMF), hexamethlyphosphoric-triamide (HMPA) and mixtures thereof. Alternatively, a salt such as the potassium or sodium salt of an acid of formula I is reacted with a halide such as the bromide or chloride of an alcohol of formula II, III or IV or the mesylate or tosylate of the alcohol to form a carboxylic ester of formula A.

The thiolesters of formula A (W is sulfur) can be prepared by the reaction of a thiol, otherwise corresponding to the alcohols of formula II, III and IV, with an acid halide of an acid of formula I. Alternatively, the thiolesters can be synthesized by reaction of the salt such as the sodium salt of a thioacid corresponding to the acid of formula I with a halide such as the bromide or the mesylate corresponding to an alcohol of formula II, III or IV.

The benzothiophene-2-carboxylic acids and benzothiophene-3-carboxylic acids of formula I can be prepared by the reaction of a nitrobenzaldehyde with a lower alkyl thioglycolate to form the lower alkyl benzothiophene carboxylate using the method of Beck, *J. Org. Chem.* 37, 3224 (1972) which is converted into the benzothiophene acetic acid via the reaction of the benzothiophene carboxylic acid halide with $CH_2N_2$ and silver oxide. The benzothiophene acetic acid is converted into an acid of formula I by alkylation with a halide, $R^1X$ such as the iodide, using an amide reagent.

The following terms, wherever used in the description herein and the appended claims, have the meaning defined below, unless otherwise specified hereinafter.

The term "lower alkyl" refers to an alkyl group, straight or branched, having a chain length of one to six carbon atoms. The term "lower haloalkyl" refers to an alkyl group substituted with one to three halogen atoms such as chloromethyl, fluoromethyl, trifluoromethyl, 2,2,2,-trifluoroethyl, 6-chlorohexyl, 2-fluoroethyl, and the like. The term "lower alkoxy" refers to an alkoxy group, straight or branched, having a chain length of one to six carbon atoms. The term "lower haloalkoxy" refers to an alkoxy group substituted with such as dichloromethoxy, trifluoromethoxy, difluoromethoxy, and the like.

The term "lower alkenyl" refers to an ethylenically unsaturated hydrocarbon group, straight or branched, having a chain length of two to six carbon atoms and one ethylenic bond such as vinyl, 3-butenyl, 2-hexenyl, i-propenyl, and the like.

The compounds of the present invention of formula (A) have one or more asymmetric carbon atoms. The present invention includes each of the optical isomers and racemic mixtures thereof. In the examples hereinafter, unless otherwise specified, the compound prepared is a racemic mixture.

The compounds of the present invention of formula A are useful pest control agents, particularly for the control of insects and acarids. In the use of the compounds of formula A for combating insects and acarids for the protection of agricultural crops, for example soybeans, cotton, alfalfa, etc., a compound of formula A, or mixtures thereof, together with a carrier is applied to the locus in a pesticidally effective amount. The carrier can be liquid or solid and include adjuvants such as wetting agents, dispersing agents and other surface active agents. The compounds of formula A can be used in formulations such as wettable powders, solutions, dusts, granules, emulsifiable concentrates, and the like. Suitable solid carriers include natural and synthetic silicates and clays, carbon or charcoal granules, natural and synthetic resins, waxes, and the like. Suitable liquid carriers include water, aromatic hydrocarbons, alcohols, vegetable and mineral oils, ketones, and the like. The amount of a compound of formula A in the formulation can vary widely, generally within the range of about 0.01 percent to about 90.0 percent, by weight.

The compounds of the present invention are effective on many different insects and on acarids. The compounds are effective control agents for insects such as mosquitoes, flies, aphids, weevils and acarids such as the spider mite and ticks. Depending upon the particular combination of the substituents of formula A herein, the compounds have a broad or relatively narrow spectrum of unusually high pesticidal activity on insects and acarids. Among the pests against which the compounds of the present invention are pesticidally effective are insects of the order Lepidoptera, Orthoptera, Heteroptera, Homoptera, Diptera, Coleoptera or Hymenoptera, and acarids of the order Acarina including mites of the family Tetranychidae or Tarsonemidae and ticks such as Ornithodoros.

The compounds of the present invention can be used in combination with other pesticides such as the carbamates, phosphates and insect growth regulators, e.g. propoxur, carbaryl, naled, dichlorvos, methoprene, kinoprene, hydroprene, cyhexatin, resmethrin, permethrin and fenvalerate.

The following examples are provided to illustrate the practice of the present invention. Temperature is given in degrees centigrade. RT means room temperature.

EXAMPLE 1

(A) A mixture of benzothiophene-2-carboxylic acid (2.5 g, 14.0 mmol), oxalyl chloride (2.0 g, 16 mmol), 25 ml of benzene and 0.3 ml of DMF is stirred for about 1.5 hours. The benzene solution is decanted off and solvent removed to give the acid chloride of benzothiophene-2-carboxylic acid.

(B) The acid chloride in about 30 ml of ether is added to a solution of $CH_2N_2$ (generated from 15 ml of 40% KOH and 4 g of N-methylnitrosomethylurea) in about 150 ml of ether at ice bath temperature. The reaction mixture is allowed to stand overnight and then carefully stripped of solvent. The solid product is dissolved in 100 ml of absolute ethanol, gently heated to 40° and a suspension of $Ag_2O$ in 100 ml of ethanol added in small portions over about 1 hour. The mixture is heated to reflux for 1 hour, cooled, filtered through Celite and KOH (1 g.) in 60 ml of water added. The mixture is heated to reflux for 3 hours. The reaction is cooled, solvent stripped, take up in 100 ml water and washed with ether. The aqueous phase is then acidified and extracted with ether. The combined ether extracts are dried and solvent removed to yield benzothiophene-2-acetic acid.

(C) To di-isopropylamine (1.5 g, 14.6 mmol) in 20 ml of THF/HMPA (2:1), at −40°, is added n-butyllithium (0.94 g, 14.6 mmol) in hexane dropwise. The mixture is stirred about 30 minutes and then, at −30°, benzothiophene-2-acetic acid (1.4 g, 7.3 mmol) in 10 ml of THF is added followed by stirring for 40 minutes. Then isopropyl iodide (8.0 mmol) in 10 ml THF is added at −30°. The reaction mixture is allowed to warm to ambient temperature and stirred for about 48 hours. The reaction is poured onto 100 g ice and washed with ether.

The aqueous phase is acidified, extracted with ether. The combined ether extracts are dried and solvent removed. The crude product is taken up in ether, stirred with 2 g LiBr, filtered and solvent removed to yield 2-82-benzothienyl)-3-methylbutanoic acid.

(D) A mixture of 2-(2-benzothienyl)-3-methylbutanoic acid (1 g, 4.3 mmol), 3-phenoxybenzyl bromide (1.1 g, 4.3 mmol) and $K_2CO_3$ (8.6 mmol) in 25 ml of THF/HMPA (1:1) is stirred overnight. The reaction is worked up by diluting with ether, washing with water, drying over $Na_2SO_4$, and solvent removed to yield 3-phenoxybenzyl 2-(2benzothienyl)-3-methylbutanoate which can be further purified by preparing thin layer chromatography eluting with 5 percent ether/hexane.

EXAMPLE 2

A mixture of 2-(2-benzothienyl)-3-methylbutanoic acid (0.5 g, 21.4 mmol) and $KHCO_3$ (21.4 mmol) in 10 ml THF/DMF (1:1) is stirred for 10 minutes. Then the mesylate of α-cyano-3-phenoxybenzyl alcohol (0.65 g, 21.4 mmol) in 3 ml THF is added followed by stirring overnight. The mixture is diluted with 100 ml ether, washed with water and saturated NaCl, dried and solvent stripped to yield crude product. The product is isolated using thin layer chromatography developing with 15% ethyl acetate/hexane to give α-cyano-3-phenoxybenzyl 2-(2-benzothienyl)-3-methyl-butanoate, viscous liquid.

EXAMPLE 3

A mixture of 2-(2-benzothienyl)-3-methylbutanoic acid (2.14 mmol), oxalyl chloride (2.2 mmol), 15 ml benzene and a few drops of DMF is stirred for about 45 minutes. The acid chloride is isolated by decanting and then 15 ml of benzene is added followed by dimethylaminopyridine (2.2 mmol) and α-cyano-3-(4-fluororbenzoyl)benzyl alcohol (2.14 mmol) in 5 ml benzene. The reaction mixture is stirred overnight and then worked up by diluting with ether, washed with water and saturated brine, dried and solvent removed. The product is thin layer chromatographed developing with 15% ethyl acetate/hexane to give α-cyano-3-(4-fluororbenzoyl)benzyl 2-(2-benzothienyl)-3-methylbutanoate.

To a stirred suspension of magnesium (3.6 g, 150 mmol) in 25 ml of ether is slowly added 4-fluorophenyl bromide (143 mmol) in 125 ml ether while gently refluxing. Refluxing is continued about 45 minutes after addition complete. After cooling to 3°, 3-methylphenyl nitrile (16.7 g, 143 mmol) in 20 ml ether is added slowly. The reaction mixture is allowed to rise to RT and then stirred overnight. The reaction is poured onto ice (200 g) and 50 ml 10% HCl and extracted with ether. The combined ether extracts are washed with 10% NaOH, water, 10% HCl and water, dried and solvent removed. The product is fractionally distilled to give 3-(4-fluorobenzoyl)phenylmethane 103°–105° (0.1 mm) which on reaction with N-bromosuccinimide in carbon tetrachloride, reflux about 3 hours, yields 3-(4-fluorobenzoyl)benzyl bromide. The thus-obtained bromide (12 g) is heated at 100° with NaHCO₃ (26 g) and dimethylsulfoxide (200 ml) for about 6 hours to give 3-(4-fluorobenzoyl)phenylcarboxaldehyde. The carboxaldehyde is dissolved in 40 ml ether and stirred with 150 ml saturated NaHSO₃ for about 48 hours and filtered yielding a white solid of which 3 grams is separated and treated with NaCN (1.3 g) in ether to yield α-cayno-3-(4-fluorobenzoyl)benzyl alcohol.

EXAMPLE 4

A mixture of 2-(3-benzothienyl)-3-methylbutanoic acid (3.4 mmol) and KCHO₃ (3.4 mmol) on 15 ml THF/DMF (1:1) is stirred for about 15 minutes. The mesylate of α-cyano-3-phenoxybenzyl alcohol (3.4 mmol) in 5 ml THF/DMF is added and the reaction mixture stirred for about 48 hours. The reaction is worked up as in Example 2, developing with 10% ethyl acetate/hexane to yield α-cyano-3-phenoxybenzyl 2-(3-benzothienyl)-3-methylbutanoate, colorless thick liquid.

3-(Benzothienyl)methyl chloride (15 g) is reacted with KCN (6.5 g) in 50 ml DMF to form the nitrile which on treatment with KOH (7.6 g) in ethanol/water under reflux gives benzothienyl-3-acetic acid. 2-(3-Benzothienyl)-3-methylbutanoic acid is obtained by treatment of benzothienyl-3-acetic acid with isopropyl iodide using the procedure of Example 1.

EXAMPLE 5

To lithium aluminum hydride (26.5 mmol) and 50 ml ether, at −20° under nitrogen, is slowly added methyl 5-chlorobenzothiophene-2-carboxylate (6 g, 26.5 mmol). The mixture is then stirred at −20° for 10 minutes. After no starting material is detectable by thin layer chromatography, the mixture is quenched with 1 ml water, 1 ml 15% NaOH, and 3 ml water at −20°. The mixture is allowed to warm to RT and stirred for 15 hours. The mixture was then filtered and solvent evaporated to give 5-chlorobenzothiophene-2-methanol.

To a mixture of N-chlorosuccinimide (13.1 mmol) and 50 ml toluene, at 0°, is slowly added dimethylsulfide (18.1 mmol). The mixture is stirred briefly, cooled to −25° and 5-chlorobenzothiophene-2-methanol (10. 1 mmol) added followed by stirring for 2 hours. Triethylamine (13.1 mmol) is added and the mixture allowed to warm to RT. The mixture is taken up in ether, washed with 10% HCl, water and brine, dried over sodium sulfate and solvent removed to give 5-chlorobenzothiophene-2-carboxaldehyde.

To a mixture of 30 ml THF and trimethylsilyldithiane (1.85 g, 9.65 mmol), cooled to −70°, is added n-butyllithium (6.03 ml) over about 15 minutes. The mixture is stirred at −70° for 3 hours and then 5-chlorobenzothiophene-2-carboxaldehyde (8.38 mmol) is added over about 10 minutes. The mixture is allowed to warm to RT over 1.5 hours and then stirred for 15 hours. The mixture is taken up in ether, washed with water and brine, dried over sodium sulfate and solvent removed to yield the dithiane of 5-chlorobenzothiophene-2-carboxaldehyde which is heated in HCl and acetic acid to give the acid, 5-chlorobenzothiophene-2-acetic acid. Following the procedure of Example 1(C), the acid is alkylated using diisopropyl iodide to give 2-(5-chloro-2-benzothienyl)-3-methylbutanoic acid.

A mixture of 10 ml methylene chloride, 10 ml THF, 2-(5-chloro-2-benzothienyl)-3-methylbutanoic acid (0.5 g), K₂CO₃ (0.25 g) and α-cyano-3-phenoxybenzyl chloride (0.42 g) is stirred at RT for 15 hours. Then 5 ml of DMSO is added and reaction mixture stirred for about 48 hours. The mixture is taken up in ether, washed with water and brine, dried over Na₂SO₄ and solvent removed. The crude product is plated developing with 10% ethyl acetate/hexane to give α-cyano-3-phenoxybenzyl 2-(5-chloro-2-benzothienyl)-3-methylbutanoate.

EXAMPLE 6

A mixture of 20 ml DMF, 2-(5-chloro-2-benzothienyl)-3-methylbutanoic acid (0.5 g), K₂CO₃ (0.51 g) and 3-phenoxybenzyl bromide (0.44 g) is stirred, under nitrogen, for about 15 hours. The mixture is then taken up in ether, washed with water and brine, dried over Na₂SO₄ and solvent removed. The crude product is plated developing with 10% ether/hexane to give 3-phenoxybenzyl 2-(5-chloro-2-benzothienyl)-3-methylbutanoate.

EXAMPLE 7

Following the procedures hereinabove, each of the acids under Column I is prepared and converted to the α-cyano-3-phenoxybenzyl ester under Column II.

I 2-(4-chloro-2-benzothienyl)-3-methylbutanoic acid
2-(5-fluoro-2-benzothienyl)-3-methylbutanoic acid
2-(6-chloro-2-benzothienyl)-3-methylbutanoic acid
2-(5-trifluoromethyl-2-benzothienyl)-3-methylbutanoic acid
2-(5,6-dimethoxy-2-benzothienyl)-3-methylbutanoic acid

II

α-cyano-3-phenoxybenzyl 2-(4-chloro-2-benzothienyl)-3-methylbutanoate
α-cyano-3-phenoxybenzyl 2-(5-fluoro-2-benzothienyl)-3-methylbutanoate
α-cyano-3-phenoxybenzyl 2-(6-chloro-2-benzothienyl)-3-methylbutanoate
α-cyano-3-phenoxybenzyl 2-(5-trifluoromethyl-2-benzothienyl)-3-methylbutanoate
α-cyano-3-phenoxybenzyl 2-(5,6-dimethoxy-2-benzothienyl)-3-methylbutanoate

EXAMPLE 8

To a stirred solution of α-cyano-4-fluoro-3-phenoxybenzyl alcohol (437 mg, 1.8 mmol), 2-(2-benzothienyl)-3-methylbutanoic acid (2.0 mmol) and 4-dimethylaminopyridine (0.65 mmol) in 20 ml of methylene chloride and 2 ml of dimethylformamide is added N,N'-dicyclohexylcarbodiimide (2.0 mmol). The reaction mixture is stirred, under nitrogen, for two hours and then filtered and extracted with water. The aqueous phase is extracted with ether. The combined organic phases are washed with saturated aqueous sodium bicarbonate, water and saturated aqueous sodium chloride, dried over calcium sulfate and solvent evaporated to give α-cyano-4-fluoro-3-phenoxybenzyl 2-(2-benzothienyl)-3-methylbutanoate.

α-cyano-4-fluoro-3-phenoxybenzyl 2-(5-chloro-2-benzothienyl)-3-methylbutanoate is prepared using 2-(5-chloro-2-benzothienyl)-3-methylbutanoic acid as the starting material.

EXAMPLE 9

To a stirred solution of 4-fluoro-3-phenoxybenzyl alcohol (0.22 g, 0.99 mmol) and triethylamine (0.14 g, 1.38 mmol) in ether (about 15 ml), under nitrogen, is added by syringe a solution of the acid chloride of 2-(5-chloro-2-benzothienyl)-3-methylbutanoic acid (1.5 mmol) in ether. The mixture is stirred for about 1 hour and then quenched with saturated aqueous sodium bicarbonate. The ether phase is washed with aqueous sodium bicarbonate, water and brine and filtered through silica. Evaporation of solvent, followed by thin layer chromatography, gives 4-fluoro-3-phenoxybenzyl 2-(5-chloro-2-benzothienyl)-3-methylbutanoate.

Following the above procedure, 2-fluoro-5-phenoxylbenzyl 2-(5-chloro-2-benzothienyl)-3-methylbutanoate is prepared using 2-fluoro-5-phenoxylbenzyl alcohol in place of 4-fluoro-3-phenoxybenzyl alcohol. Similarly, using each of 3-(4-fluorophenoxy)-4-fluorobenzyl alcohol and 2-fluoro-5-(4-fluorophenoxy) benzyl alcohol as the alcohol starting material, there is prepared 3-(4-fluorophenoxy-4-fluorobenzyl 2-(5-chloro-2-benzothienyl)-3-methylbutanoate and 2-fluoro-5-(4-fluorophenoxy) benzyl 2-(5-chloro-2-benzothienyl)-3-methylbutanoate, respectively.

EXAMPLE 10

To a stirred solution of cyano (6-phenoxy-2-pyridyl) methanol (1.8 mmol), 2-(5-chloro-2-benzothienyl)-3-methylbutanoic acid (2.0 mmol) and dimethylaminopyridine (2.0 mmol) in 20 ml of methylene chloride and 2 ml of DMF is added N,N'-dicyclohexylcarbodiimide (2.0 mmol). The reaction mixture is stirred, under nitrogen, for two hours and then filtered and extracted with water. The aqueous phase is extracted with ether. The combined organic phases are washed with saturated aqueous NaHCO₃, water and saturated aqueous NaCl, dried over CaSO₄ and solvent evaporated to yield cyano(6-phenoxy-2-pyridyl) methyl 2-(5-chloro-2-benzothienyl)-3-methylbutanoate.

Similarly, each of 2-(5-fluoro-2-benzothienyl)-3-methylbutanoic acid, 2-(6-chloro-2-benzothienyl)-3-methylbutanoic acid and 2-(2-benzothienyl)-3-methylbutanoic acid is converted into
cyano(6-phenoxy-2-pyridyl)methyl 2-(5-fluoro-2-benzothienyl)-3-methylbutanoate
cyano(6-phenoxy-2-pyridyl)methyl 2-(6-chloro-2-benzothienyl)-3-methylbutanoate and
cyano(6-phenoxy-2-pyridyl)methyl 2-(2-benzothienyl)-3-methylbutonoate

EXAMPLE 11

To a mixture of 2-(5-chloro-2-benzothienyl)-3-methylbutanoic acid (2.63 mmol), cold methylene chloride (5 ml) and dimethylaminopyridine (0.21 mmol) is added, at 0°, α-methyl (6-phenoxy-2-pyridyl) methanol (2.79 mmol) in 2 ml of methylene chloride and then dicyclohexylcarbodimiide (2.61 mmol). The reaction mixture is stirred at RT for about 4 hours and then worked up as in Example 10 to give α-methyl(6-phenoxy-2-pryidyl)methyl 2-(5-chloro-2-benzothienyl)-3-methylbutanoate.

The alcohol, α-methyl(6-phenoxy-2-pyridyl) methanol is prepared by Grignard reaction of 6-phenoxypyridyl-2-carboxaldehyde and methylmagnesium bromide in tetrahydrofuran. 6-Phenoxy2-pyridylmethanol reacted with chromium trioxide in pyridine and methylene chloride gives 6-phenoxypyridyl-2-carboxaldehyde.

EXAMPLE 12

To a stirred solution of (6-phenoxy-2-pyridyl) methanol (0.2 g, 0.99 mmol) and triethylamine (0.14 g, 1.38 mmol) in ether (about 15 ml), under nitrogen, is added by syringe a solution of the acid chloride of 2-(5-chloro-2-benzothienyl)-3-methylbunanoic acid (1.5 mmol) in ether. The mixture is stirred for about 30 minutes and then quenched with saturated aqueous sodium bicarbonate. The ether phase is washed with aqueous NaHCO₃, water and brine and filtered through silica. Evaporation of solvent gives the (6-phenoxy-2-pyridyl) methyl ester of 2-(5-chloro-2-benzothienyl)-3-methylbutanoic acid.

EXAMPLE 13

A. To a cooled solution, about 5°, of 2-(5-chloro-2-benzothienyl-3-methylbutanoic acid (3.38 mmol) in 25 ml of DMF is added triethylamine (3.38 mmol) and ethyl chloroformate (3.38 mmol). The reaction mixture is stirred for about 15 minutes and then sodium hydrosulfide (6.76 mmol) and 10 ml of DMF are added. The mixture is stirred at 5° for about 1.5 hours. The reaction is worked up by adding ether and then acidifying with 5% H₂SO₄. The ether layer is washed with water and brine, dried over sodium sulfate and solvent evaporated to give the thioacid of 2-(5-chloro-2-benzothienyl-3-methylbutanoic acid.

B. To 15 ml of DMF and 10 ml of THF is added 1.60 mmol of the thioacid of part A, KHCO₃ (4.01 mmol) and the mesylate of α-cyano-(6-phenoxy-2-pyridyl) methanol (1.60 mmol). The reaction mixture is stirred at RT for about 18 hours. The mixture is taken up in ether, washed with water and brine, dried over sodium sulfate and solvent stripped to give S-α-cyano-(6-phenoxy-2-pyridyl)methyl thioester of 2-(5-chloro-2-benzothienyl)-3-methylbutanoic acid.

EXAMPLE 14

Following the procedure of Example 12, the acid chloride of each of 2-(2-benzothienyl)-3-methylbutanoic acid and 2-(5-fluroo-2-benzothienyl-3-methylbutanoic acid is reacted with (6-benzoyl-2-pyridyl) methanol to yield (6-benzoyl-2-pyridyl) methyl 2-(2-benzothienyl)-3-methylbutanoate and (6-benzoyl-2-pyridyl)methyl 2-(5-fluoro-2-benzothienyl)-3-methylbutanoate.

To 15 g of 6 -methyl-2-pyridylcarboxylic acid (122 mmol) in 200 ml benzene is added dropwise 19.1 g (150 mmol) oxalyl chloride (dissolved in 30 ml benzene) with ice bath cooling. After 1 hr, solvent and excess chloride are removed. Concentrate is taken up in 100 ml benzene, cooled to ~10° & 175 mmol AlCl₃ added. The solution is heated to 25° for 1 hour, then heated to reflux for 2 hours, and finally cooled and stirred overnight. The mixture is poured onto ice/conc. HCl, then washed with ether. Fifty Percent (50%) sodium hydroxide is added until the precipitate is dissolved. The solution is extracted with CHCl₃, washed with water, dried and stripped, leaving 6-benzoyl-2-methylpyridine.

The 6-benzoyl-2-methylpyridine (3.9 g, 21 mmol), in 20 ml CHCl₃, is added over 1 hour to 4.2 g (21 mmol) m-chloroperbenzoic acid (in 50 ml CHCl₃). The temperature is kept below 25° as the mixture is stirred overnight. The reaction is diluted with CHCl₃, washed with sat. NaHSO₃, water, 20% NaHCO₃ (2×) and then water, dried, stripped and finally titrated with hexane/ethyl acetate to give 6-benzoyl-2-methylpyridine N-oxide.

Acetic anhydride (6.6 ml) is heated to 115°, after which 6-benzoyl-2-methylpyridine N-oxide is added in portions over 1 hour. The mixture is then held at 115° for 1 hour after the addition. The reaction is poured onto ice and extracted with ether (3×). The combined ether phases are washed with sat. NaNCO₃ (2×) and water until neutral, dried and stripped. The product is preparatory thin layer chromatographed, the least polar band giving 2-(acetoxymethyl)-6-benzoylpyridine.

Potassium hydroxide (1.1 g, 18 mmol) is dissolved in 25 ml methanol, after which is added 2-(acetoxymethyl)-6-benzoylpyridine (2.3 g, 9 mmol) in 20 ml methanol and the mixture is then stirred overnight. The mixture is diluted with water and saturated sodium chloride, then extracted with ether (2×), washed with sat. sodium chloride, dried over magnesium sulfate and stripped to yield (6-benzoyl-2-pyridyl)methanol.

EXAMPLE 15

A mixture of (6-benzoyl-2-pyridyl)methanol (1.5 g, 7 mmol), potassium hydroxide (1.3 g, 23 mmol) and hydrazine 85% (1 ml, 25 mmol) in triethylene glycol (10 ml) is refluxed for 1½ hours, and then the water and excess hydrazine are removed by a takeoff condenser until the temperature rises to 195°-200°. After 4 hours at 195°-200°, the solution is cooled, poured into ice and water (50 ml) and extracted with ether (3×20 ml). The combined ether layers are washed with water (3×20 ml), brine (10 ml) and dried over calcium sulfate. Removal of solvents gives (6-benzyl-2-pyridyl)methanol.

Following the procedure of Example 12, the acid chloride of each of 2-(2-benzothienyl)-3-methylbutanoic acid and 2-(5-chloro-2-benzothienyl)-3-methylbutanoic acid is reacted with (6-benzyl-2-pyridyl)methanol to yield (6-benzyl-2-pyridyl)methyl 2-(2-benzothienyl)-3-methylbutanoate and (6-benzyl-2-pyridyl)methyl 2-(5-chloro-2-benzothienyl)-3-methylbutanoate.

EXAMPLE 16

The acid chloride of 2-(5-chloro-2-benzothienyl)-3-methylbutanoic acid is reacted with cyano[6-(3-fluorophenoxy)-2-pyridyl]methanol and cyano[4-(4-fluorophenoxy)-2-pyridyl] methanol using the procedure of Example 12 to give cyano[6-(3-fluorophenoxy)-2-pyridyl] methyl 2-(5-chloro-2-benzothienyl)-3-methylbutonate and cyano[6-(4-fluorophenoxy)-2-pyridyl] methyl 2-(5-chloro-2-benzothienyl)-3-methylbutanoate.

EXAMPLE 17

Each of 2-(2-benzothienyl)-3-methylbutanoic acid and 2-(5-fluoro-2-benzothienyl)-3-methylbutanoic acid is reacted with α-methyl (6-phenoxy-2-pyridyl)methanol to give α-methyl (6-phenoxy-2-pyridyl)methyl 2-(2-benzothienyl)-3-methylbutanoate and α-methyl (6-phenoxy-2-pyridyl)methyl 2-(5-fluoro-2-benzothienyl)-3-methylbutanoate.

EXAMPLE 18

To 2-(2-benzothienyl)-3-methylbutanoic acid (3 mmol) in benzene is added 5 mmol of oxalyl chloride, and DMF at RT. After about 5 minutes, the solution is warmed to about 40°, stripped of solvent and excess oxalyl chloride. Then to the acid chloride in THF is added (6-phenoxy-2-pyridyl)methylthiol (3.2 mmol) and dimethylaminopyridine with stirring. The reaction mixture is stirred for about 18 hours and then worked up in ether, washing with water and brine, drying over sodium sulfate and solvent removed to give S-(6-phenoxy-2-pyridyl) methyl thioester of 2-(2-benzothienyl)-3-methylbutanoic acid.

The thiol, (6-phenoxy-2-pyridyl) methylthiol, is prepared by the reaction of (6-phenoxy-2-pyridyl)methyl bromide with thioacetic acid using sodium hydride to form the thiolester which is then converted to the desired thiol using lithium aluminum hydride.

Using the procedure of Example 10, (6-phenylthio-2-pyridyl)methanol is reacted with 2-(5-chloro-2-benzothienyl)-3-methylbutanoic acid to give (6-phenylthio-2-pyridyl)methyl 2-(5-chloro-2-benzothienyl)-3-methylbutanoate.

EXAMPLE 19

The alcohol, cyano [6-(3,4-dimethoxyphenyl)-2-pyridyl] methanol and cyano [6-(2-fluorophenoxy)-2-pyridyl]methanol, is reacted with the acid chloride of 2-(5-chloro-2-benzothienyl)-3-methylbutanoic acid to yield cyano[6-(3,4-dimethoxy-phenoxy)-2-pyridyl]methyl 2-(5-chloro-2-benzothienyl-3-methylbutanoate and cyano[6-(2-fluorophenoxy)-2-pyridyl]methyl 2-(5-chloro-2-benzothienyl)-3-methylbutanoate.

EXAMPLE 20

To a stirred solution of 3-benzylpyrrolylmethyl alcohol (0.99 mmol) and triethylamine (0.14 g, 1.38 mmol) in ether (about 15 ml), under nitrogen, is added a solution of the acid chloride of 2-(5-chloro-2-benzothienyl)-3-methylbutanoic acid (1.5 mmol) in either. The mixture is stirred for about 60 minutes and then quenched with saturated aqueous NaHCO₃. The ether phase is washed with aqueous NaHCO₃, water and brine, dried over sodium sulfate and solvent evaporated to give 3-benzylpyrrolylmethyl 2-(5-chloro-2-benzothienyl)-3-methylbutanoate.

EXAMPLE 21

To the acid chloride of 2-(2-benzothienyl)-3-methylbutanoic acid (2.5 mmol) in ether is added 1.3 ml of triethylamine followed by 3-benzylpyrrolymethyl alcohol (2.0 mmol) in ether over about 2 minutes. The reaction mixture is stirred for about 18 hours and then quenched with saturated aqueous sodium bicarbonate. The organic phase is washed with aqueous NaHCO₃, water and brine, dried over CaSO₄ and solvent evaporated to give 3-benzylpyrrolylmethyl 2-(2-benzothienyl)-3-methylbutanoate.

EXAMPLE 22

To a stirred solution of 3-benzylpyrrolyl methanol (1.8 mmol), 2-(5-fluoro-2-benzothienyl)-3-methylbutanoic acid (2.0 mmol) and 4-dimethylaminopyridine (2.0 mmol) in 20 ml of methylene chloride and 2 ml of DMF is added N,N'-dicyclohexylcarbodiimide (2.0 mml). The reaction mixture is stirred, under nitrogen, for about two hours and then filtered and extracted with water. The aqueous phase is extracted with ether. The combined organic phases are washed with saturated aqueous NaHCO₃, water and saturated aqueous NaCl, dried over CaSO₄ and solvent evaporated to yield 3- benzylpyrrolylmethyl 2-(5-fluoro-2-benzothienyl)-3-methylbutanoate.

EXAMPLE 23

The acid chloride of 2-(5-chloro-2-benzothienyl)-3-methylbutanoic acid is reacted with 3-(4-fluorobenzyl)-pyrrolylmethyl alcohol in ether as in Example 20 to give 3-(4-fluorobenzyl)-pyrrolylmethyl 2-(5-chloro-2-benzothienyl)-3-methylbutanoate.

EXAMPLE 24

2-(6-Chloro-2-benzothienyl)-3-methylbutanoic acid (3.40 mmol) is stirred together with 0.34 g (3.40 mmol) KHCO$_3$ in 10 ml THF/DMF (1:1) for 15 minutes. Then 3.40 mmol of 3-benzylpyrrolylmethyl methanesulfonate in 5 ml THF/DMF (1:1) is added and the mixture stirred for approximately 48 hours. The reaction is diluted with ether, washed with water (3×) and sat. NaCl, dried and solvent is removed to yield 3-benzylpyrrolylmethyl 2-(6-chloro-2-benzothienyl)-3-methylbutanoate.

EXAMPLE 25

A mixture of 2-(5-trifluoromethyl-2-benzothienyl)-3-methylbutanoic acid (3.95 mmol), thionyl chloride (0.342 ml, 4.74 mmol) and DMF (several drops) in 50 ml benzene is stirred at RT for 2 days. The solvent and excess thionyl chloride are evaporated under reduced pressure. The resulting acid chloride is dissolved in 50 ml benzene, and 3-benzylpyrrolylmethyl alcohol (3.95 mmol) and 0.482 g 4-dimethylaminopyridine (3.95 mmol) are added. The mixture is left at 25° for 18 hours and then heated under reflux for 2 hours. The mixture is then poured into water and extracted with ether. The organic phase is washed with dilute HCL, sat. NaHCO$_3$, water and brine, dried and solvent removed under vacuum to yield 3-benzylpyrrolylmethyl 2-(5-trifluoromethyl-2-benzothienyl)-3-methylbutanoate.

EXAMPLE 26

Each of 2-(5-methyl-2-benzothienyl)-3-methylbutanoic acid and 2-(5-methoxy-2-benzothienyl)-3-methylbutanoic acid is converted to α-cyano-3-phenoxybenzyl 2-(5-methyl-2-benzothienyl)-3-methylbutanoate and α-cyano-3-phenoxybenzyl 2-(5-methoxy-2-benzothienyl)-3-methylbutanoate using the procedure of Example 2.

Under IUPAC rules, the term "benzo [b] thiophene" is designated for the group—

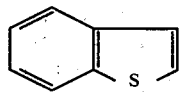

Herein, for convenience and brevity, said term is shortened to "benzothiophene."

Two groups of 10 each of 0.24 hour III instar Heliothis virescens larvae were treated with 1μl of the compound, α-cyano-3-phenoxybenzyl 2-(5-chloro-2-benzothienyl)-3-methylbutanoate, in acetone at five different concentrations by application to the dorsum of the thorax. Two groups of 10 each are treated individually with 1μl acetone only as controls. Larvae are held individually in 30 ml plastic cups provided with artificial medium for 72 hours at 25° and 16 hour photoperiod. After 72 hours the number of dead is calculated as a percentage of the total number originally treated and then corrected for any mortality in the control groups using Abbott's formula. The LC$_{50}$ of the compound was less than 0.1%.

What is claimed is:

1. A compound of the following formula (A):

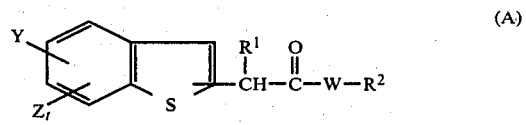

wherein,

W is oxygen or sulfur; t is zero, one, two, or three; each of Y and Z is, independently, selected from hydrogen, bromo, chloro, fluoro, lower alkyl, lower alkoxy, lower haloalkoxy and lower haloalkyl; R$^1$ is lower alkyl, lower alkenyl or lower cycloalkyl;

R$^2$ is selected from the groups,

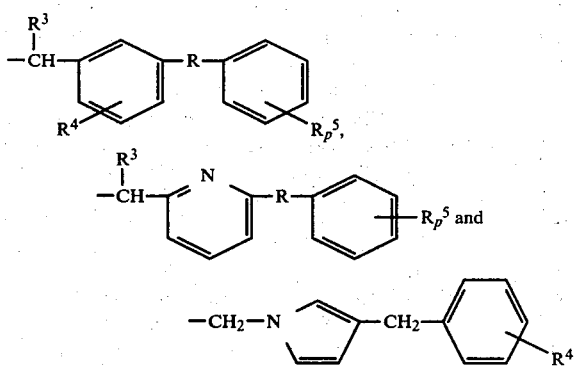

R is oxygen, sulfur, methylene or carbonyl;
R$^3$ is hydrogen, cyano, ethynyl, methyl, ethyl, or trifluoromethyl;
R$^4$ is hydrogen or fluoro;
R$^5$ is hydrogen, bromo, chloro, fluoro, methyl, methoxy, or trifluoromethyl; and
p is zero, one or two.

2. A compound according to claim 1 of the following formula:

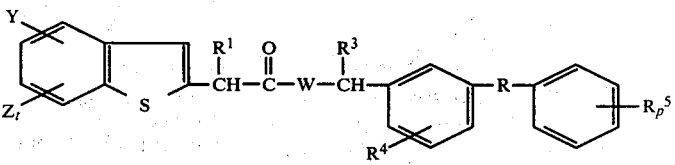

3. A compound according to claim 2 wherein W is oxygen; t is zero or one; and R$^1$ is isopropyl.

4. A compound according to claim 3 wherein R is oxygen, R$^3$ is hydrogen or cyano, R$^4$ is hydrogen and p is zero or one.

5. A compound according to claim 4 wherein t is zero and Y is in position 5 or 6.

6. A compound according to claim 5 wherein Y is hydrogen, chloro, fluoro, methyl, methoxy or trifluoromethyl and p is zero.

7. The compound, α-cyano-3-phenoxybenzyl 2-(5-chloro-2-benzothienyl)-3-methylbutanoate, according to claim 6.

8. A compound according to claim 3 wherein R is oxygen, $R^3$ is hydrogen or cyano; $R^4$ is fluoro; and p is zero or one.

9. A compound according to claim 8 wherein t is zero, Y is in position 5 or 6, Y is hydrogen, chloro, fluoro, methyl, methoxy or trifluoromethyl; and $R^5$ is hydrogen or fluoro.

10. A compound according to claim 9 wherein $R^4$ is in position 2 or 4 and $R^5$ is fluoro in position 3 or 4.

11. A compound according to claim 1 of the following formula:

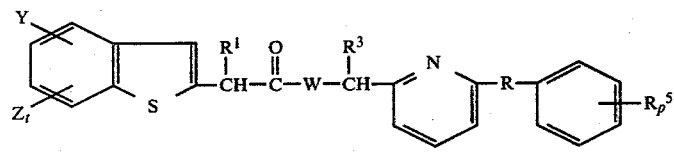

12. A compound according to claim 11 wherein $R^1$ is isopropyl and t is zero or one.

13. A compound according to claim 12 wherein $R^3$ is hydrogen, cyano or methyl.

14. A compound according to claim 13 wherein t is zero, Y is in the 5 or 6 position, Y is hydrogen, chloro, fluoro, methyl, methoxy or trifluoromethyl, and p is zero or one.

15. A compound according to claim 14 wherein W is oxygen.

16. A compound according to claim 15 wherein R is oxygen and p is zero.

17. A compound according to claim 15 wherein R is oxygen and $R^5$ is chloro or fluoro in the 3 or 4 position.

18. A compound according to claim 14 wherein W is sulfur.

19. A compound according to claim 18 wherein R is oxygen and $R^5$ is hydrogen, chloro or fluoro in the 3 or 4 position.

20. A compound according to claim 15 wherein $R^3$ is methyl.

21. A compound according to claim 18 wherein $R^3$ is methyl.

22. A compound according to claim 1 of the following formula:

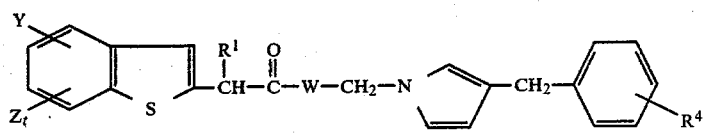

23. A compound according to claim 22 wherein $R^1$ is isopropyl and t is zero or one.

24. A compound according to claim 23 wherein W is oxygen and Y is hydrogen, chloro, fluoro, methyl, methoxy or trifluoromethyl.

25. A compound according to claim 24 wherein Y is in the 5 or 6 position, $R^4$ is in the 3 or 4 position and t is zero.

26. A compound according to claim 25 wherein $R^4$ is hydrogen.

27. A compound according to claim 25 wherein Y is in the 5 position.

28. A process for the control of insects or acarids which comprises applying an insecticidally or acaricidally effective amount of a compound of formula (A) as defined herein, to said insects or acarids or the locus thereof.

* * * * *

Notice of Adverse Decision in Interference

In Interference No. 100,910, involving Patent No. 4,224,330, C. A. Henrick, J. N. Labovitz, M. M. Leippe and S. L. Woo, ESTERS AND THIOLESTERS OF BENZOTHIENYL ACIDS, final judgment adverse to the patentees was rendered Jan. 4, 1984, as to claims 1–10 and 28.

[*Official Gazette March 13, 1984.*]